United States Patent [19]
Shieh

[11] Patent Number: 5,447,617
[45] Date of Patent: Sep. 5, 1995

[54] COATED CAPILLARY COLUMNS AND ELECTROPHORETIC SEPARATION METHODS FOR THEIR USE

[75] Inventor: Chia-Hui Shieh, Irvine, Calif.

[73] Assignee: Beckman Instruments, Inc., Fullerton, Calif.

[21] Appl. No.: 186,736

[22] Filed: Jan. 25, 1994

[51] Int. Cl.6 .................................................. C25B 7/00
[52] U.S. Cl. ................................ 204/299 R; 204/182.8
[58] Field of Search ......................... 204/182.8, 299 R

[56] References Cited

U.S. PATENT DOCUMENTS

| | | | |
|---|---|---|---|
| 4,680,201 | 7/1987 | Hjerten | 427/230 |
| 5,192,406 | 3/1993 | Woolley | 204/299 R |
| 5,221,447 | 6/1993 | Hjerten | 204/299 R |
| 5,282,941 | 2/1994 | Rose, Jr. | 204/299 R |
| 5,322,608 | 6/1994 | Karger et al. | 204/299 R |

OTHER PUBLICATIONS

Hjerten, Stellan; "High-Performance Electrophoresis Elimination of Electroendosmosis and Solute Adsorption"; Journal of Chromatography; vol. 347 (1985); pp. 191-198.

Article by Fridstrom, Anita. M. and Markides, Karin. E.; "Synthesis of a Bondable Dense Deactivation Layer for Capillary Electrophoresis"; Jan. 1993.

Schmalzing, Dieter, Piggee, Christine A., Foret, Frantisek, Carrilho, Emanuel and Karger, Barry L.; "Characterization and performance of a neutral hydrophilic coating for the capillary electrophoretic separation of biopolymers"; Journal of Chromatography A; vol. 652 (1993); pp. 149-159.

Primary Examiner—John Niebling
Assistant Examiner—C. Delacroix-Muirheid
Attorney, Agent, or Firm—William H. May; Paul R. Harder; Janis C. Henry

[57] ABSTRACT

Coated capillary electrophoresis columns and methods for their use in electrophoretic separations are disclosed. The coated capillary columns include a length of tubing having an interior surface having an interconnected polymeric coating. The interconnected polymeric coating includes a hydrophobic polymeric functionality covalently bound to the interior surface and a hydrophilic polymer interconnected with the hydrophobic polymeric functionality. Exemplary columns are prepared by causing a Si-OH reactive compound, having a hydrophobic polymeric functionality, to react with Si-OH functionalities on the interior surface of capillary columns. Then causing a hydrophilic monomer to polymerize in contact with the hydrophobic polymeric functionality forms a coating of interconnecting hydrophilic and hydrophobic polymers.

20 Claims, 5 Drawing Sheets

COATED CAPILLARY COLUMNS AND ELECTROPHORETIC SEPARATION METHODS FOR THEIR USE

BACKGROUND OF THE INVENTION

1. Field of the Invention

The present invention relates generally to capillary columns having interior surface coatings and electrophoretic separation methods for their use. More particularly, the present invention involves capillary columns having a neutral crosslinked hydrophilic coating on their interior wall surfaces. The neutral crosslinked hydrophilic coating reduces analyte interaction with the interior surface of the capillary column and simultaneously protects the interior surface of the capillary column during the electrophoretic separation of acidic and basic compounds.

2. Description of Relevant Art

Electrophoretic separation techniques have been utilized for years to separate molecules according to differences in the effective charge of the molecules, and/or according to differences in the molecular size of the molecules. Up until recently electrophoretic separations were conducted in gel slabs or open gel beds which were typically fabricated of polyacrylamide gel material. More recently capillary electrophoresis techniques combined with photometric detection methods have allowed the automation and rapid quantitative analysis of molecules. High resolution separations of molecules having different effective charges have been achieved by applying electrophoretic principles to buffer filled or gel filled narrow capillary tubes.

Typically, capillary columns used in capillary electrophoresis are fabricated of lengths of silica tubing having diameters on the order of 25 $\mu$m to 200 $\mu$m and lengths from about 10 to 200 cm. The buffer and gel separation mediums are pumped directly into the column interiors and electrophoretic techniques are used to separate numerous types of molecules including peptides, proteins, and oligonucleotides, nucleic acids and other charged molecular species. The field of electrophoretic separation technology is continually expanding with respect to the types and sizes of molecules which can be separated and detected using capillary electrophoresis procedures.

The advantages associated with capillary electrophoresis are numerous. Quantitative information can be achieved with very small sample sizes, and the amount of gel or buffer consumed is minuscule. Furthermore, the time required for the separations is sharply reduced, and the technique lends itself to automation and electronic data storage and data manipulation. Significantly, capillary electrophoresis is associated with certain phenomenon which are not present in traditional slab gel electrophoresis. One of these is the now familiar electroosmotic flow phenomenon characterized by bulk flow of buffer solutions toward one of the electrodes.

Electroosmotic flow is generated by the ionization of silanol functionalities on the surface of silica capillary tubing. The ionization results in a layer of protons in the electrophoretic buffer solution at the surface of the silica tubing. In the presence of an electric field the layer of protons resembles a positively charged column of fluid which migrates toward the cathode, causing a general bulk movement of the buffer medium. Advantageously, electroosmotic flow can be utilized in many applications to improve electrophoretic separations. For example, when the electrophoretic migration of the molecules being separated is in the opposite direction to that of electroosmotic flow, the net effect is an increase in column performance and improved separations.

For many electrophoretic applications electroosmotic flow is undesirable and eliminating or substantially reducing the bulk flow is preferred. Generally, when electroosmotic flow is reduced to a minimum, electrophoretic sample components move only by electrophoretic migration, which improves analysis reproducibility and mass recovery of sample components.

One method to minimize or to control electroosmotic flow, is to utilize capillary columns fabricated of silica capillary tubing coated on the inside with a polymeric material. The polymeric coating eliminates or substantially reduces the degree of ionization of the surface silanol groups which causes at least a substantial reduction in the bulk flow within the electrophoresis column. In order to avoid unwanted hydrophobic-hydrophobic interactions between sample components and the coating, the polymeric coatings are traditionally hydrophilic. One problem associated with the hydrophilic polymeric coatings is their low physical integrity, their tendency to dislodge from the surface of the capillary, and the resulting short useful life. Covalently binding hydrophilic polymers to the surface of the capillary tubing, helps reduce the coating's tendency to dislodge, however the physical integrity of the coatings remains a problem.

Additionally, even when covalently bound to the surface of silica capillaries through an Si-O-Si, hydrophilic coatings promote aqueous interaction with Si-O-Si functionalities. This can result in the unwanted hydrolysis and the Si-O-Si bond and a resulting shorted use life time.

As mentioned above, another problem associated with capillary electrophoresis techniques is the tendency for sample components to adhere to the wall of the capillary tubing, and in particular silica tubing. This is especially true in the case of small charged molecules which are easily attracted to reactive silica functionalities. When small peptides and amines are present in electrophoretic separation mediums, they interact both electrostatically and hydrophobically with the capillary wall. The result is a decrease in separation efficiency and undesirable band broadening which gives erroneous separation data.

Like electroosmotic flow, providing electrophoresis capillaries which are capable of minimizing the degree of sample component and wall interaction have not been totally successful. Previous attempts include using a dynamic double layer coating. These bilayer coatings are not stable and require additives in the running buffers used during the electrophoretic process. Hydrophobic coatings are effective in protecting the Si-O-Si surfaces of silica columns, but cause unwanted hydrophobic-hydrophobic interactions between the capillary wall and analytes. As noted above, hydrophilic coatings are not effective in protecting the Si-O-Si surface.

Accordingly, it is an objective of the present invention to provide novel coated capillary columns useful for electrophoresis separations and which minimize electroosmotic flow.

It is additionally an objective of the present invention to provide capillary columns which reduce or eliminate interactions between sample components and the interior capillary wall.

It is further an objective of the present invention to provide capillaries having physically stable coatings.

It is additionally an objective of the present invention to provide capillaries useful for the electrophoretic separation of a variety of charged molecules.

SUMMARY OF THE INVENTION

The present invention satisfies the above-identified objectives by providing capillary columns having interior surface coatings which contribute to the elimination or substantial reduction in the amount of interaction between sample constituents and the interior surface of the capillary column. The coated capillary columns of the present invention additionally contribute to minimizing of the degree of electroosmotic flow during electrophoretic separations, thereby eliminating bulk flow and restricting sample movement to electrophoretic migration. Advantageously, use of the capillary columns of the present invention results in improved separations for a number of acidic and basic compounds including amines, amino acids, peptides, and proteins. Moreover, the polymeric coatings described herein have considerable physical integrity and are highly stable, making the useful life of the columns substantially improved over prior art columns.

More particularly, the capillary columns of the present invention include a length of tubing having an interior surface. The interior surface has a crosslinked polymeric coating which includes a hydrophobic polymeric functionality covalently bound to the interior surface of the capillary tubing and a hydrophilic polymer copolymerized with the hydrophobic polymeric functionality. Preferably, the capillary tubing used to prepare the column is fabricated of silica and the hydrophobic polymeric functionality is covalently bound to the interior surface by a Si-O-Si bond which are formed by reacting the capillary surface Si-OH functionalities with a suitable reactant. In preferred embodiments the hydrophobic polymeric functionality is polybutadiene and the hydrophilic polymer is polyacrylamide.

The coated capillary columns of the present invention can be prepared by providing a length of silica tubing having an interior surface and Si-OH functionalities on the interior surface and causing a Si-OH reactive compound to react with Si-OH functionalities. Suitable Si-OH reactive compounds include silane and siloxane compounds having at least one neutral hydrophobic functionality and preferably the hydrophobic functionality is polymeric and capable of further reacting with polymerizable monomers. Then, causing a hydrophilic monomer to homopolymerize and react with the hydrophobic functionality, results in an interconnected polymeric coating of hydrophilic and hydrophobic polymers. In preferred processes the reactive compound is a polymeric polybutadienenyl triethoxy silane and the hydrophilic monomer is acrylamide.

Also disclosed herein are methods for preparing and methods for using the coated capillary columns of the present invention. More particularly, in accordance with the present invention a method for preparing a coated capillary column includes the steps of providing a length of silica tubing having an interior surface and Si-OH functionalities on the interior surface and causing a Si-OH reactive compound to react with the Si-OH functionalities, the Si-OH reactive compound having a hydrophobic polymeric functionality. Then causing a hydrophilic monomer to polymerize in contact with the hydrophobic polymeric functionality, results in an interconnecting polymeric network of hydrophilic and hydrophobic polymers. The interconnecting polymeric network has high physical integrity and extended useful life.

These and other advantages associated with the present invention will become apparent to those skilled in the art upon an understanding the invention as described in the detailed description of the invention taken in combination with the following drawings.

DETAILED DESCRIPTION OF THE INVENTION

The present invention provides coated capillary columns which are particularly useful in electrophoretic separation systems such as the P/ACE series Capillary Electrophoresis Systems manufactured and sold by Beckman Instruments, Inc., Fullerton, Calif. More specifically, the coated capillary columns of the present invention are useful as separation mediums in applications in which a variety of molecular species are separated on the basis of their electrophoretic mobility. These molecular species include basic and acidic macromolecules such as proteins and polynucleotides as well as smaller compounds such as basic drugs and nucleic acids.

The coated capillary columns described herein contribute to eliminating or substantially minimizing electroosmotic flow during electrophoretic separations. As a feature of the present invention, the coating materials used for forming the coated columns are compounds joined by covalent bonds to each other and to the wall of the capillary column, thus forming an interconnecting polymeric network. This results in coatings having enhanced physical integrity which in turn provides columns with longer useful lives and improved reliability and precision in electrophoretic separation procedures. The enhanced physical integrity and the chemical properties of the coatings also contribute to a prolonged ability to prevent the interaction of different analytes with the wall of the capillary column.

The coated capillary columns of the present invention incorporate hydrophilic polymeric properties in the coating and thus substantially eliminate hydrophobic interactions between sample components and the capillary wall. Additionally, the capillary columns of the present invention incorporate hydrophobic functionalities covalently bonded to the surface of the capillary column. These hydrophobic properties reduce the interaction of the aqueous electrophoresis buffer environment with the interior wall of the capillary, thus minimizing hydrolysis of the covalently bound coating from the wall of the capillary tubing.

Figure 1:
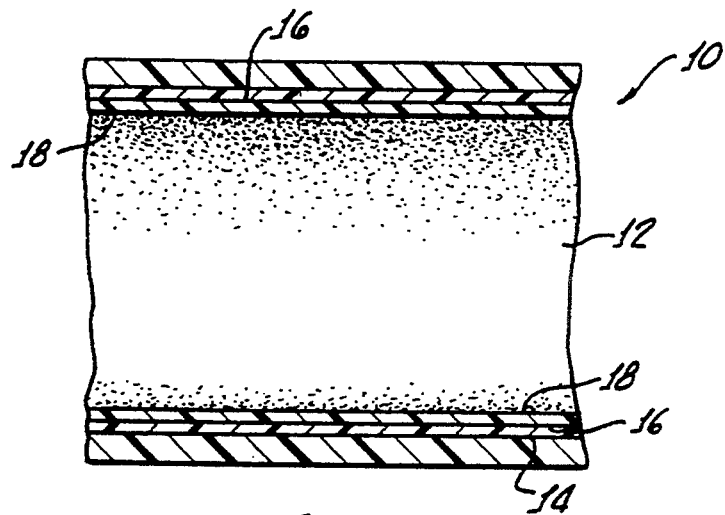
FIG. 1 is a cross-sectional view of capillary electrophoresis column of the present invention illustrating a crosslinked hydrophobic polymer and hydrophilic polymer coating on the interior surface of a silica capillary column.

More particularly, and referring to a representative partial longitudinal cross-sectional view of a column shown in FIG. 1, the coated capillary columns 10 of the present invention are fabricated of a length of capillary tubing 12 having an interior surface 14. The interior surface 14 has an interconnected polymeric coating which includes a hydrophobic polymeric functionality 16 covalently bound to the interior surface 14 of the capillary tubing 12 and a hydrophilic polymer 18 bonded to the hydrophobic polymeric functionality 16.

Capillary tubing 12 suitable for use in the present invention can be fabricated from organic polymeric materials such a polyacrylates, polyvinyls, polymethacrylates or inorganic materials which include silica, quartz. Preferably, the selected organic or inorganic material has chemical moieties, or can be altered to have chemical moieties, which react under mild pH and temperature conditions with compounds having hydrophobic functionalities so that the hydrophobic polymeric functionality 16 is covalently bonded to the surface of the capillary tubing. As illustrated in FIG. 1, the hydrophobic polymeric functionality 16 additionally is capable of reacting with a hydrophilic compound 18 which is either a polymer or is polymerizable, thus providing a coating of a crosslinked network of hydrophobic polymer and hydrophilic polymer.

The preferred material for fabricating capillary columns useful in the present invention is silica. Silica capillary columns have been used for decades in chromatography procedures and more recently have found utility in electrophoresis procedures. Accordingly, the fabrication and handling of these columns are credited to those skilled in the art and will not be discussed in greater detail herein. As discussed in more detail in the context of the present invention, advantageously, silica has Si-OH functionalities which readily react with compounds such as siloxanes and similarly reactive silanes. Since siloxanes and silanes having a variety of different chemical substituents are widely available commercially, their use in combination with silica columns is particularly advantageous in the practice of the present invention.

In accordance with the present invention, preferred compounds having hydrophobic functionalities and capable of covalently bonding to the surface of the capillary tubing are silane or siloxane compounds with polymeric hydrocarbon moieties. Such hydrocarbon containing compounds are preferably additionally capable of reacting with selected hydrophilic monomers or hydrophilic polymers. This additional capability allows the formation of a bonded interconnecting network of hydrophobic polymers and hydrophilic polymers on the capillary interior surface. Accordingly, preferred hydrophobic polymeric hydrocarbon moieties are reactive hydrocarbons such as polybutadiene. Those skilled in the art will appreciate that these hydrocarbons have reactive vinyl moieties for reacting with vinyl hydrophilic monomers. Moreover, vinyl hydrophilic monomers can be polymerized in the presence of such vinyl containing hydrocarbons and react with the vinyl containing hydrocarbons to form a network of hydrophilic polymers covalently linked to hydrophobic polymeric functionalities which are in turn covalently bonded to the wall of the capillary tubing.

Thus, in preferred embodiments of the present invention, compounds having hydrophilic functionalities are vinyl containing hydrophilic monomers and the compounds having hydrophobic functionalities are silanes or siloxanes modified to carry polybutadiene moieties which are capable of reacting with the vinyl hydrophilic monomers. Those skilled in the art will appreciate that once polymerized, the result is a homopolymerized and copolymerized network of hydrophobic polymeric functionalities and hydrophilic polymeric functionalities. The resulting coated electrophoresis capillary column has a substantially reduced amount of Si-OH functionalities on the interior surface of the capillary tubing. Thus, electroosmotic flow or bulk flow within the column while under the influence of an electric field is substantially eliminated. Moreover, the hydrophobic polymeric functionality bonded to the surface of the column reduces aqueous electrophoretic buffer interactions with the covalent bond formed to covalently link the coating. This reduced interaction eliminates hydrolysis of the covalent bond, which is typically an Si-O-Si bond, and contributes to an increased useful column life. Finally, the hydrophilic polymeric portion of the coating shields the electrophoresis analytes from the hydrophobic portions of the coating, thereby eliminating unwanted hydrophobic-hydrophobic interactions between sample analyte components and the coating or capillary wall.

Those skilled in the art will appreciate that a variety of compounds having hydrophobic hydrocarbon functionalities and a variety of hydrophilic monomeric compounds are suitable in the practice of the present invention. In addition to polybutadiene modified silanes or siloxanes (including polysilanes and polysiloxanes), virtually any vinyl containing hydrocarbon modified silane or siloxanes can be used. In particular, polybutadiene functionalities provided on reactive polysiloxanes or polysilanes having a wide range of molecular weights are useful. These molecular weights range from 200 to over 2,000,000. The limiting factor in the molecular weight is the length of the polybutadiene chain which can cause steric hindrance and may interfere with bonding the silane or siloxane to the surface of the capillary column. Because these compounds have reactive vinyl functionalities, they are capable of copolymerizing with hydrophilic vinyl monomers including hydroxyethylmethacrylate, vinylpyrrolidone, acrylamides, and others to form a coating network which includes a hydrocarbon hydrophobic polymeric layer and a second network of hydrophilic polymeric layers. Similarly, esters capable of transesterification reactions on the surface of acrylate capillary tubing and having vinyl hydrocarbon functionalities can copolymerize with hydrophilic monomers to form similar networks.

Referring again to FIG. 1, in preferred embodiments of the present invention, capillary tubing 12 is fabricated of silica and, depending upon the particular analytical application, can vary in length and in diameter. Typically the column will be from between about 10 cm to 200 cm in length and from 25–200 $\mu$m in inner diameter. Advantageously, the surface of silica capillary tubing has SiOH moieties which are reactive with a number of organic and inorganic chemical functionalities and provide reactive sites for covalently attaching compounds having desirable chemical characteristics to the interior wall surface 14 of the capillary tubing 12. Further, and in accordance with preferred embodiments of the present invention, the hydrophobic chemical functionalities 16 are polybutadiene functionalities which are attached to the interior wall surface 14 via Si-O-Si bonds generated by the reaction of a siloxane with SiOH functionalities. In this preferred embodiment, the hydrophilic polymer 18 is polyacrylamide, which, when formed by polymerizing acrylamide monomer in the presence of suitable initiators will also copolymerize with residual and free vinyl groups of the polybutadiene and contribute to the formation of the crosslinked polymeric coating.

Figure 2:
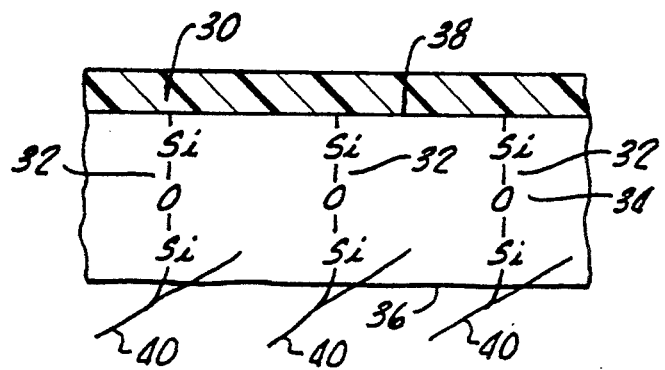
FIG. 2 is a partial cross-sectional view of capillary electrophoresis column illustrating a preferred embodiment of the present invention.

The partial longitudinal cross-sectional view of FIG. 2, illustrating one wall of a capillary column graphically shows the preferred coated column. More particularly, the coating of the preferred capillary column 30 of the present invention is a crosslinked polymeric network which is covalently bonded via a Si-O-Si 32 bond to the interior wall surface 38 of the capillary tubing 34. Polybutadiene forms a hydrophobic coating layer 36 adjacent the capillary interior wall surface 38 and polyacrylamide forms a hydrophilic outer layer 40 which is available for interacting with sample components and the aqueous buffer systems utilized in electrophoretic separations. Furthermore, the polyacrylamide acts as a bridge between lengths of polyacrylamide thereby forming a crosslinked network of polymers. Those skilled in the art will appreciate that the hydrophobic characteristics of the above-described coating minimizes the interaction of the aqueous buffer with the capillary wall surface. More particularly, hydrophobic-hydrophilic repulsions preclude interaction between aqueous media and the coating interface at the capillary wall surface, thereby eliminating hydrolysis of the SiOH bond. Thus, the polymeric coating network remains covalently bound to the capillary interior wall surface and contributes to a substantial increase in the useable life of the capillary column.

Another feature of the preferred coated capillary column of the present invention is the hydrophilic characteristics of the coating. As shown in FIG. 1 and FIG. 2, the hydrophilic portion of the coating is available for interaction with the buffer system utilized during electrophoretic separations. Additionally, the hydrophilic polymeric portion acts as a buffer zone between the hydrophobic portion of the coating and the buffer media. This hydrophilic polymeric buffer prevents hydrophobic-hydrophobic interactions between the coating and electrophoretic sample components and thus minimizes sample absorption onto the surface of the capillary column.

In accordance with the present invention, processes for preparing coated capillary columns include the general steps of providing a length of silica tubing having an interior surface with Si-OH functionalities on the interior surface and then causing a siloxane compound to react with the Si-OH functionalities. The siloxane compound is further characterized as having a neutral polymerizable functionality which provides reactive sites for crosslinking or copolymerization with monomers which are reactive with the polymerizable functionality. When hydrophilic monomer is made available for copolymerization with the polymerizable functionality the result is a crosslinked coating of hydrophilic and hydrophobic polymers.

Prior to causing the siloxane to react with the SiOH functionalities, it is preferable to first prepare the interior surface of the capillary by successively washing the surface with an inorganic acid, an inorganic base and finally with a volatile lower organic alcohol. Causing the silane to react with the SiOH functionalities typically involves simply contacting the interior surface of the capillary with a suitable silane compound, such as polybutadieneyl triethoxy silane. The use of a inert gas under pressure, such as helium at about 10 psi, enhances the effectiveness and reduces the length of time required to contact the silane with the interior wall of the capillary column. As known in the art, the silane functionality readily reacts with SiOH moieties to form Si-O-Si bonds. Once the silane compound is secured to the interior wall of the capillary tubing, a hydrophilic monomeric compound is brought into contact with the covalently bound silane compound. As already mentioned, the hydrophilic monomeric compound is characterized by its hydrophilicity and its ability to react with a hydrophobic functionality on the covalently bound silane compound. In preferred embodiments the hydrophilic monomer is acrylamide which readily homopolymerizes and copolymerizes with the vinyl functionalities of polybutadiene. Those skilled in the art are credited with applying standard polymerization chemistry techniques known in the art for polymerizing acrylamide under conditions in which the acrylamide reacts with the vinyl functionalities available on the polybutadiene.

In the most preferred embodiments of the present invention the polyacrylamide formed during the polymerization step is further crosslinked in order to enhance the physical integrity of the coating material. Standard crosslinking methodologies can be utilized including the use of divinyl monomers such as N,N'-methylene-bis-acrylamide during the polymerization step. An alternative crosslinking method involves utilizing formaldehyde in post-polymerization crosslinking step. The two aldehyde protons of formaldehyde are available for reacting with the acrylamide protons and when the reacted acrylamide protons are located on different polyacrylamide strands, they become crosslinked. Those skilled in the art are credited with applying techniques for crosslinking acrylamide. Additionally, examples of conditions for crosslinking are provided below in the form of working examples.

Following the homopolymerization of the hydrophilic monomer and the coreaction of the hydrophilic monomer with the hydrophobic polymeric functionality, excess polyacrylamide and acrylamide is removed from the interior of the capillary column using a water wash under pressure. The coated column is then suitable for use in a variety of electrophoretic separations.

The coated capillary columns of the present invention are easily formed and adapted for use in any capillary electrophoresis system. Moreover, their use requires no special handling procedures and typical electrophoretic techniques apply to their use. Accordingly, once positioned in standard capillary electrophoresis equipment, the columns of the present invention can be used in processes for analyzing sample compositions for sample constituents by capillary electrophoresis. In accordance with the present invention, these processes typically include the steps of immersing one end of the coated capillary column in an anodic reservoir and immersing a second end of the coated column in a cathodic reservoir. Then, introducing a sample composition into the interior of the coated column at one end and applying an electric field across the reservoirs will cause the sample constituents to differentially migrate within the capillary column. When a suitable detector, for example a uv-visible detector or fluorescence detector, is appropriately positioned at least one end of the coated column, the separated sample constituents are detected and an electropherogram is generated.

Having now generally described the invention, the same will be more readily understood through reference to the following examples which are provided by way of illustration, and are not intended to be limiting of the present invention, unless specified.

EXAMPLE 1

The following illustrates exemplary first steps for the preparation of a coated capillary column of the present invention for use in electrophoresis procedures. These first steps involve preparing the interior surface of a capillary column and covalently bonding modified hydrophobic polybutadiene functionalities to the prepared interior surface.

A fused silica capillary column having a length of 65 cm and a diameter of 50 μm (available from Polymicron of Phoenix, Ariz.) was prepared for the initial reaction by rinsing the interior surface walls with a solution of 1N HCl for 15 minutes. The rinsing action was achieved by pumping the HCl solution through the capillary tubing. Next HCl solution was removed from the capillary tubing and the interior surface was rinsed in the same manner with 1N NaOH for 15 minutes. Finally, after removing the NaOH solution, the capillary interior was rinsed with methanol for 15 minutes.

After removing residual methanol solution from the capillary tubing, the prepared tubing was rinsed with a 50% toluene solution of a triethoxysilyl modified polybutadiene (50% polybutadienenyl triethoxy silane in toluene purchased from HulsAmerica, Inc. Piscataway, N.J. The polybutadienenyl triethoxy silane is a polymeric compound having multiple reactive triethoxy silane functionalities bonded to polymeric polybutadiene. As known in the art, the polybutadiene functionality has pendant vinyl groups which are reactive under vinyl polymerization conditions. The polybutadienenyl triethoxy silane solution had a viscosity of 25–50 centistokes which is an indication of its molecular weight.

The rinsing step was carried out for 30 minutes after which the two open ends of the capillary tubing were capped with silicon plugs and the capped tubing was allowed to stand for 24 hours.

EXAMPLE 2

The following example illustrates the final steps in preparing a coated capillary column of the present invention. Generally, preparing this coated capillary column involves utilizing the polybutadiene bonded interior wall column prepared as described in Example 1 and synthesizing linear polyacrylamide in the presence of the bonded polybutadiene. The result is a layer of hydrophilic linear polyacrylamide surrounding the bonded hydrophobic polybutadiene coating.

The polybutadiene bonded capillary column described in Example 1 was prepared. Then following the 24 hour aging period, the polybutadiene bonded capillary tubing was rinsed with toluene for 30 minutes. After 30 minutes, the residual toluene was removed and the capillary tubing was rinsed with methanol for 15 minutes. Next, a 5% aqueous solution of acrylamide, available from ICN Biomedical, Inc., Irvine, Calif., was prepared. The solution was degassed for 30 minutes under 100 mbar vacuum to reduce the solution oxygen content. Simultaneous with degassing the 5 wt. % acrylamide solution, a separate 100 Ml volume of water was deoxygenated by bubbling helium through the water to reduce the oxygen content below 10% of the original oxygen content. Three minutes prior to removing the 5 wt. % aqueous acrylamide solution from vacuum, the deoxygenated water was utilized to prepare a solution of 10 wt. % N,N,N',N'-tetramethylenediamine (TEMED), purchased from ICN Biochemicals, Irvine, Calif., and a solution of 10 wt. % ammonium persulfate (APS), purchased from ICN Biochemicals.

Then, immediately, 10 μL of the 10 wt. % TEMED solution and 10 μL of the 10 wt. % APS solution were added to 2 Ml of the degassed acrylamide solution to form a polymerization mixture. This polymerization mixture was pushed into the polybutadiene bonded capillary tubing using 10 psi of helium pressure. Following a 3 minute reaction period, the 10 psi helium pressure was removed and two minutes later, the two ends of the capillary tubing were capped and the tubing was allowed to stand for 24 hours. Next the end caps were removed and residual polyacrylamide which was not reacted with the polybutadiene and residual acrylamide were pushed from the capillary column interior using water at 100 psi. The result was a thin layer of linear polyacrylamide coreacted with residual vinyl groups on the bonded polybutadiene. The coated capillary column prepared according to the foregoing procedure was ready for use in capillary electrophoresis separations.

EXAMPLE 3

The following example is illustrative of a procedure for preparing an alternative coated capillary column of the present invention. The coated column described below differs from the coated column described in Example 2 in that the hydrophilic portion of the coating is a crosslinked polyacrylamide. The crosslinked polyacrylamide provides the coating with increased physical integrity and a resulting longer and more useful life.

To prepare this alternative coating, the polybutadiene bonded capillary column described in Example 1 was prepared. Then following the 24 hour aging period, the polybutadiene bonded capillary tubing was rinsed with toluene for 30 minutes. After 30 minutes, the residual toluene was removed and the capillary tubing was rinsed with methanol for 15 minutes. Then, a 5 wt. % aqueous acrylamide solution was prepared and degassed as described in Example 2. Sufficient N,N'-methylene-bis-acrylamide was added to the degassed 5 wt. % acrylamide solution to make the solution 1 wt. % N,N'-methylene-bis-acrylamide. Then a 10 wt. % aqueous TEMED and 10 wt. % aqueous APS solution were prepared as described in Example 2. A polymerization solution was prepared by adding 10 μL of the TEMED solution and 10 μL the APS solution to 2 mL of the acrylamide and N,N'-methylene-bis acrylamide solution. This polymerization solution was brought into contact with a capillary column, prepared as described in Example 1, by pushing the solution under 10 psi of helium for 2 minutes followed by reducing the helium pressure to 0 psi. Four minutes was allowed to elapse and the polymerization solution was pushed a second time under the same conditions and for the same length of time. This procedure was repeated four additional times and the capillary was rinsed with double distilled and ionized water following the following cycle. The resulting capillary column incorporated a coating which included a layer of polybutadiene covalently bonded to the interior surface of the capillary through a Si-O-Si bond and a network of crosslinked polyacrylamide which additionally reacted with residual vinyl groups of the polybutadiene. The resulting coating was securely attached to the interior wall of the capillary tubing and was additionally provided with enhanced physical integrity through the crosslinked network.

EXAMPLE 4

The following example is illustrative of a procedure for preparing a second alternative coated capillary column of the present invention. The coated column described below differs from the coated column described in Example 2 in that the hydrophilic portion of the coating is a crosslinked polyacrylamide. The coated column differs from the column described in Example 3 in that the crosslinked polyacrylamide was formed utilizing different crosslinking reagents and procedures. The crosslinked polyacrylamide provides the coating with increased physical integrity and a resulting longer and more useful life.

To prepare this alternative coating, the polybutadiene bonded capillary column described in Example 1 was prepared. Then following the 24 hour aging period, the polybutadiene bonded capillary tubing was rinsed with toluene for 30 minutes. After 30 minutes, the residual toluene was removed and the capillary tubing was rinsed with methanol for 15 minutes. When, a 5 wt. % aqueous acrylamide solution was prepared and degassed as described in Example 2. The solutions of TEMED and APS and the polymerization solution were prepared as described in Example 2. Following the preparation of these solutions the polymerization solution was forced into a capillary column, prepared as described in Example 1, under the same conditions as described in Example 2. After the acrylamide polymerized to form a linear polymer and the residual polyacrylamide which did not react with polybutadiene and excess acrylamide were removed from the column, the coated column was filled with a 37% formaldehyde solution having 2% 1N NaOH. The formaldehyde solution was allowed to stand in the column for 24 hours after which the capillary column was washed with double distilled water. The resulting coated column was suitable for electrophoretic separations of a number of different types of compounds.

EXAMPLE 5

The following illustrates exemplary applications for the coated capillary columns of the present invention. In particular, as described below, the coated columns of the present invention are useful in the separation of small charged particles such as nucleic acids.

Figure 3:
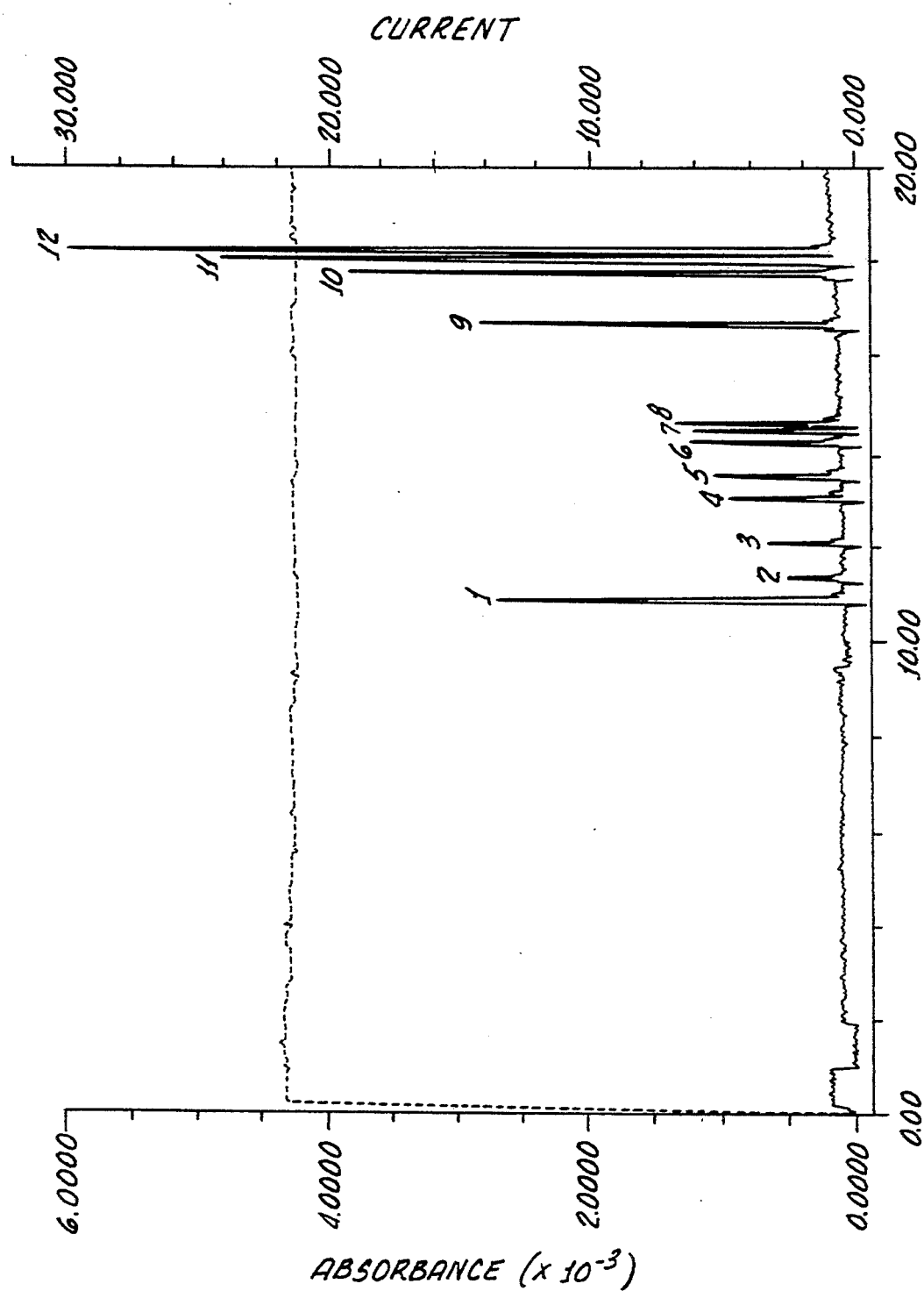
FIG. 3 is an electropherogram resulting from the electrophoretic separation of the HaIII digestion of $\phi$X174 DNA.

A 30/37 cm (37 cm overall and 30 cm to uv window) coated capillary prepared as described in Example 2 above was positioned in a P/ACE capillary electrophoresis instrument (manufactured by Beckman Instruments, Inc., Fullerton, Calif.). The column was filled with a buffer which included 3% acrylamide in 50 mM tris-HCl and 2 mM EDTA. A sample of HaIII digested $\phi$X174 DNA (200 $\mu$g/mL DNA) solution, containing an internal standard of orange G, was injected into one end of the colunm using a 10 sec 0.5 PSI pressure injection and 200 V/cm or 7.4 kV was applied across the electrophoresis reservoirs at a temperature of 20° C. The separated basic DNA fragments were detected with a uv detector at 254 nm. FIG. 3 shows the electropherogram which was obtained after less than 20 minutes of migration. Each of the DNA fragments was separated from the other DNA fragments by a baseline separation with the order of migration being the following: 1st peak: internal standard Orange G; 2nd peak: 72 base pair DNA fragment; 3rd peak: 188 base pair; 4th peak: 194 base pair; 5th peak: 234 base pair; 6th peak: 271 base pair; 7th peak: 281 base pair; 8th peak: 310 base pair; 9th peak: 603 base pair; 10th peak: 872 base pair; 11th peak: 1078 base pair; 12th peak: 1353 base pairs.

EXAMPLE 6

Figure 4:
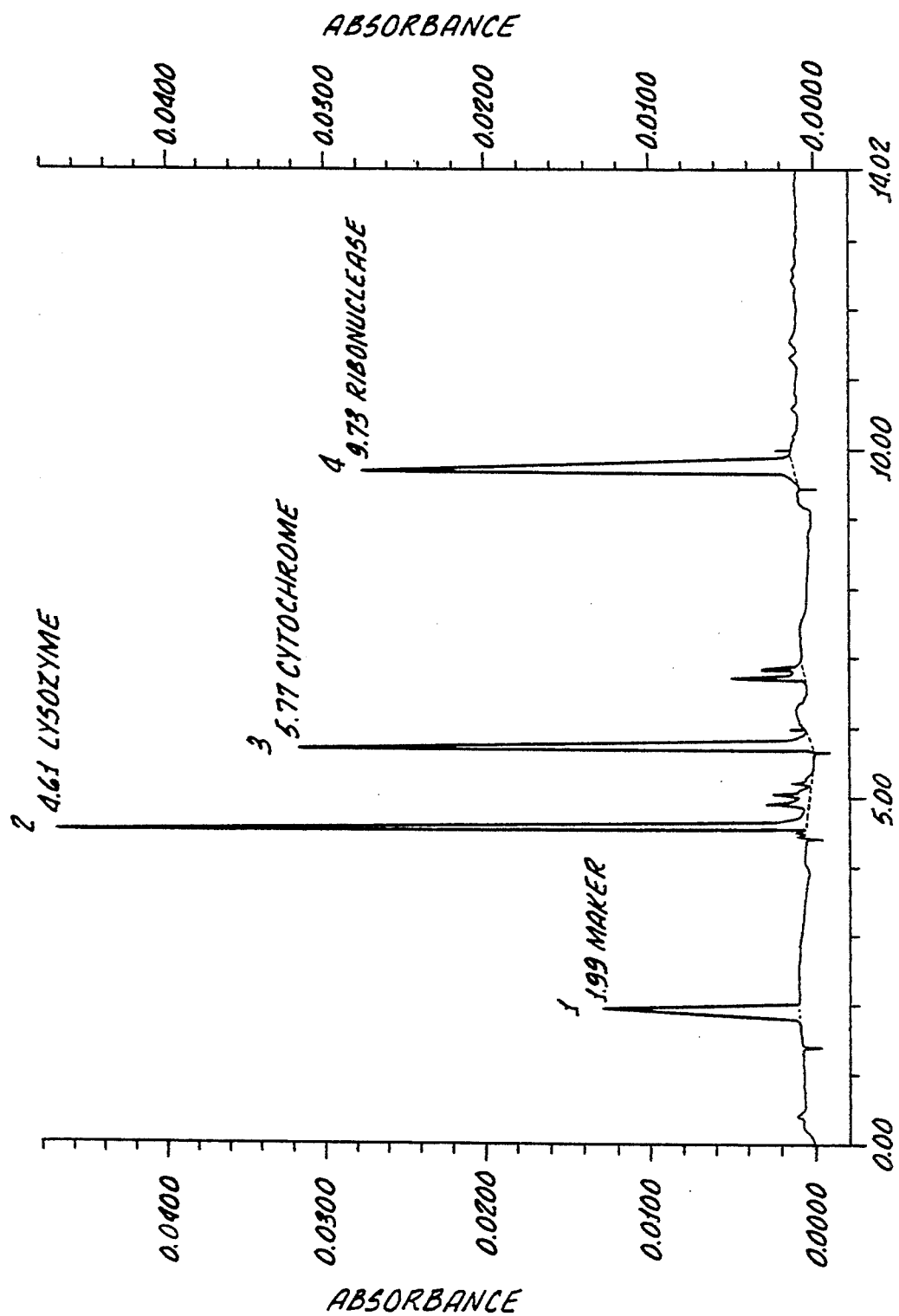
FIG. 4 is an electropherogram resulting from the electrophoretic separation of proteins in an aqueous solution in accordance with the present invention.

The following illustrates an exemplary application for the coated capillary columns of the present invention. In particular, as described below and shown in FIG. 4, the coated columns of the present invention are useful in the separation of proteins. An aqueous solution containing 1 mg/mL each of an internal standard (histamine), lysozyme, cytochrome C and ribonuclease A was prepared and a 20/27 cm coated capillary column prepared according to the procedures described in Example 4 above was placed in a P/ACE capillary electrophoresis instrument (manufactured by Beckman Instruments, Inc., Fullerton, Calif.). The column was filled with a 20 mM MES (buffer purchased from Sigma Chemical, St. Louis, Mo.) and 20 mM citrate buffer adjusted to a pH of 6.0. A sample of the aqueous protein solution was injected into one end of the column using a 2 sec 0.5 psi pressure injection and 500 V/cm was applied across the electrophoresis reservoirs at a temperature of 25° C. The separated proteins were detected with a uv detector at 214 nm. FIG. 4 shows the electropherogram which was obtained after less than 12 minutes of migration. Each of the proteins was separated from the other proteins by a baseline separation with the migration order left to right on the electropherogram being the internal standard (histidine), lysozyme, cytochrome C and ribonuclease A.

Example 6

Figure 5:
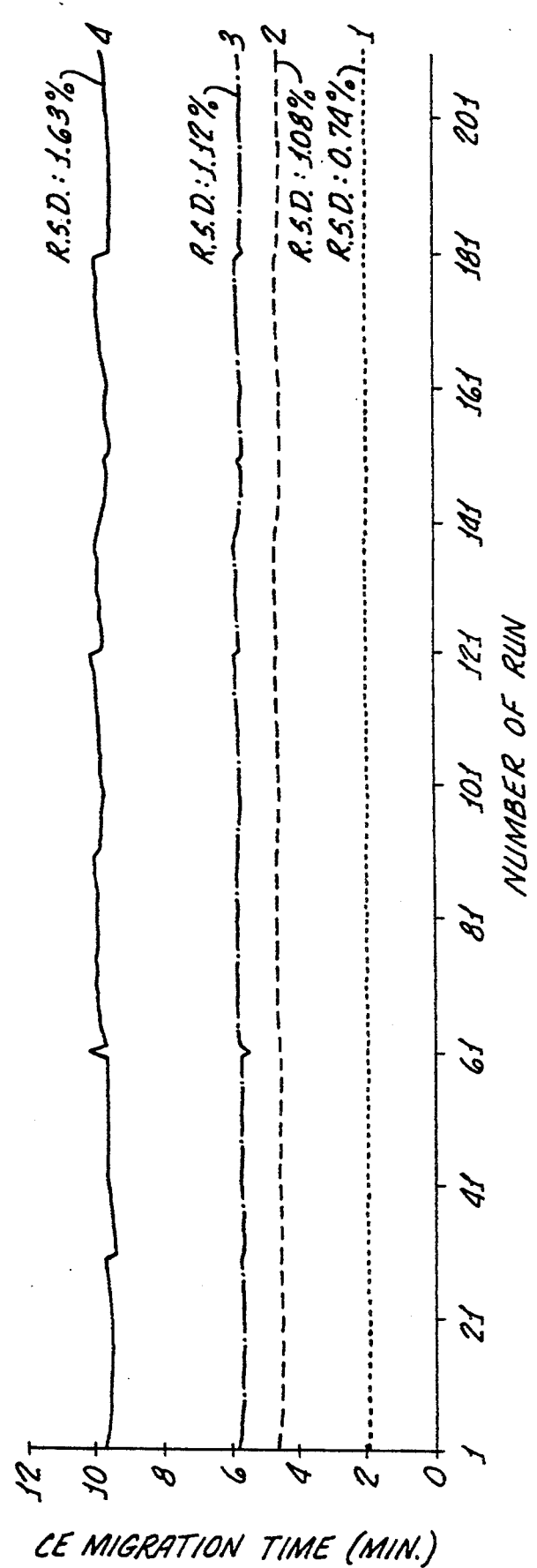
FIG. 5 illustrates the reproducibility of the electropherograms obtained using an exemplary column of the present invention.

In order to demonstrate the multi-use and long term use stability and reproducibility of assays using the coated column of the present invention, the protein assay performed in Example 5 was repeated 210 times. For each of the repeated assays the electrophoretic migration time for each protein was detected. The results of this reproducibility test are illustrated in FIG. 5. The reproducibility of the internal standard (histamine) migration time is shown at line 1 (migration time 1.99 minutes). The reproducibility of the lysozyme migration time is shown at line 2 (migration time 4.6 minutes). The reproducibility of cytochrome C migration time is shown at line 3 (migration time of 5.77 minutes). Finally, the reproducibility of the ribonuclease migration time is shown at line 4 (migration time of 9.73 minutes).

The relative standard deviations for the repeated histamine assay, lysozyme assay, cytochrome C assay, and ribonuclease assay are 0.74%, 1.08%, 1.12%, 1.63%, respectively. These data clearly demonstrate the exceptional physical stability and long term use characteristics of an exemplary column of the present invention.

Example 7

Figure 6:
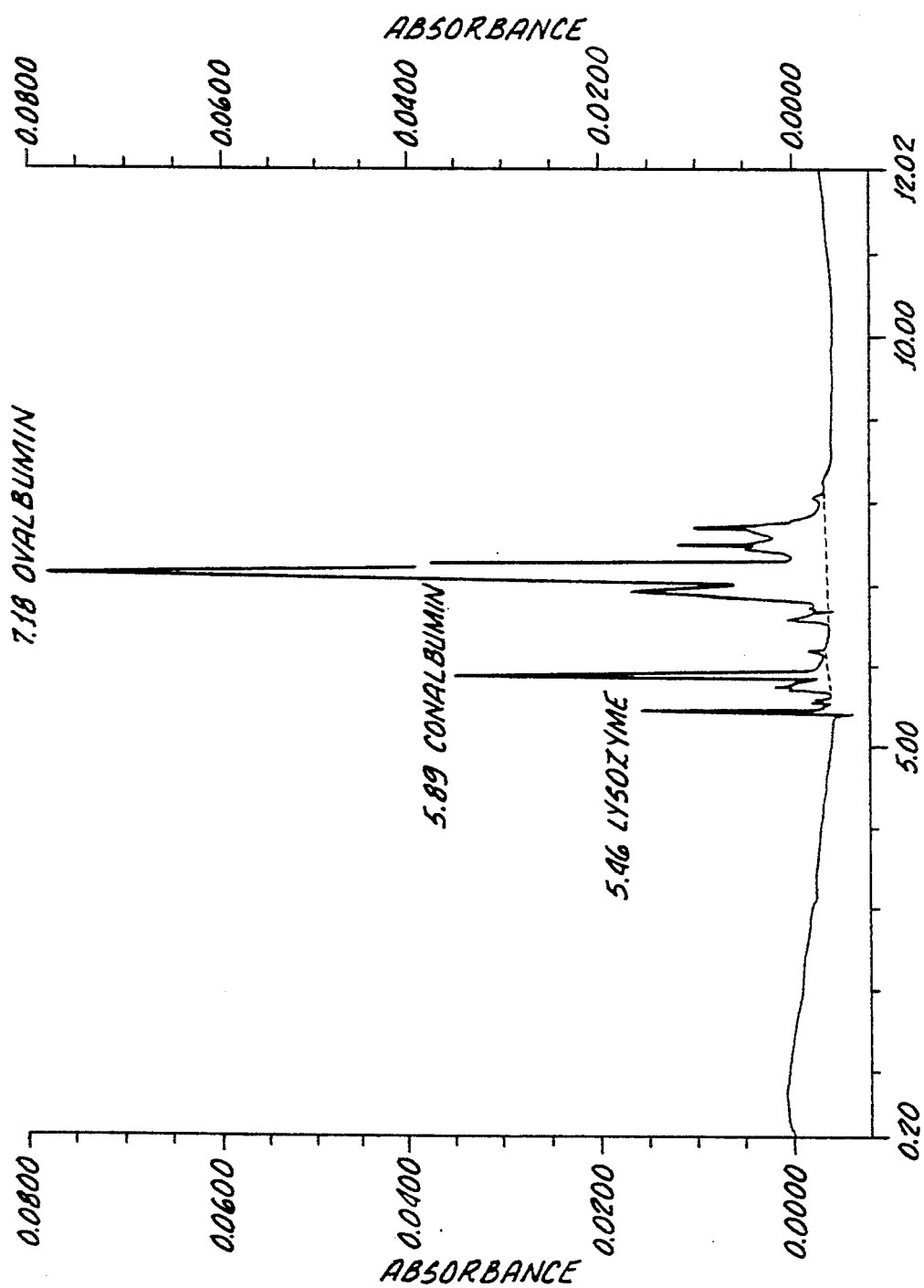
FIG. 6 is an electropherogram obtained from the electrophoretic analysis of proteins in chicken egg white.

The following example illustrates a further application of an exemplary column of the present invention. More particularly, a column prepared according to the procedure described in Example 4, was used to separate the proteins in chicken egg white. The assay conditions and sample concentration were the same as described in Example 5. The results of the assay are shown in FIG. 6. The peak at migration time 5.46 was identified as lysozyme, the peak at 5.89 as conalbumin, and the peak at 7.18 ovalbumin.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A capillary column for electrophoretic separations of sample components, said capillary column comprising:
    a length of tubing having an interior surface, said interior surface having an interconnected polymeric coating, said interconnected polymeric coating comprising a hydrophobic hydrocarbon backbone polymeric functionality covalently bound to said interior surface and a hydrophilic polymer copolymerized with said hydrophobic polymeric functionality.

2. The capillary column of claim 1 wherein said tubing is fabricated of silica and said hydrophobic hydrocarbon backbone polymeric functionality is covalently bound to said interior surface by a Si-O-Si bond.

3. The capillary column of claim 1 wherein said hydrophobic hydrocarbon backbone polymeric functionality is polybutadiene.

4. The capillary column of claim 1 wherein said hydrophilic polymer is polyacrylamide.

5. The capillary column of claim 3 wherein said polyacrylamide is crosslinked.

6. A capillary column for electrophoretic separations of sample components, said capillary column comprising:
    a length of tubing having an interior surface, said interior surface having an interconnected polymeric coating, said interconnected polymeric coating comprising a polybutadiene functionality covalently bound to said interior surface and polyacrylamide copolymerized with said polybutadiene functionality.

7. The capillary column of claim 6 wherein said capillary tubing is formed of silica and said polybutadiene functionality is covalently bound to said interior surface through a Si-O-Si bond.

8. The capillary column of claim 7 wherein said polybutadiene functionality is covalently bound to said interior surface by reacting polybutadieneyl triethoxy silane with Si-OH of said silica.

9. The capillary column of claim 6 wherein said polyacrylamide is crosslinked.

10. A process for preparing a capillary column, said process comprising the steps:
    providing a length of silica tubing having an interior surface and Si-OH functionalities on said interior surface,
    causing a Si-OH reactive compound to react with said Si-OH functionalities, said Si-OH reactive compound having a hydrophobic hydrocarbon backbone polymeric functionality;
    causing a hydrophilic monomer to polymerize in contact with said hydrophobic hydrocarbon backbone polymeric functionality, thereby forming an interconnecting polymeric network of hydrophilic and hydrophobic polymers.

11. The process of claim 10 wherein said Si-OH reactive compound is polybutadienenyl triethoxy silane.

12. The process of claim 10 wherein said hydrophilic monomer is acrylamide.

13. The process of claim 10 further including the step of crosslinking said hydrophilic polymer.

14. The process of claim 12 further including the step of polymerizing said acrylamide in the presence of N,N'-methylene-bis-acrylamide, thereby forming crosslinked polyacrylamide.

15. The process of claim 12 further including the step of contacting said polymerized acrylamide with formaldehyde, thereby forming crosslinked polyacrylamide.

16. A process for analyzing a sample composition for sample constituents by capillary electrophoresis, said process comprising the steps:
    providing a capillary electrophoresis column comprising:
    a length of tubing having an interior surface, said interior surface having an interconnected polymeric coating, said interconnected polymeric coating comprising a hydrophobic hydrocarbon backbone polymeric functionality covalently bound to said interior surface and a hydrophilic polymer copolymerized with said hydrophobic polymeric functionality;
    immersing said first end in an anodic reservoir and immersing said second end in a cathodic reservoir;
    introducing said sample composition into said length of capillary tubing at said first end or said second end; and
    applying an electric field across said reservoirs, said electric field capable of causing said sample constituents to migrate at different rates with respect to each sample constituent within said capillary column.

17. The process of claim 16 wherein said sample constituents are selected from the group consisting of basic and acid compounds.

18. The process of claim 17 wherein said tubing is fabricated of silica and said hydrophobic polymeric functionality is covalently bound to said interior surface by a Si-O-Si bond.

19. The capillary column of claim 16 wherein said hydrophobic polymeric functionality is polybutadiene.

20. The capillary column of claim 16 wherein said hydrophilic polymer is polyacrylamide.

* * * * *